United States Patent [19]

Davankov et al.

[11] Patent Number: 5,773,384
[45] Date of Patent: Jun. 30, 1998

[54] SORBENTS FOR REMOVING TOXICANTS FROM BLOOD OR PLASMA, AND METHOD OF PRODUCING THE SAME

[75] Inventors: Vadim A. Davankov; Maria P. Tsyurupa; Ludmila A. Pavlova; Dzidra R. Tur, all of Moscow, Russian Federation

[73] Assignee: White Eagle International Technologies Group, Inc., New York, N.Y.

[21] Appl. No.: 756,445

[22] Filed: Nov. 25, 1996

[51] Int. Cl.$^6$ ............................ B01J 20/26; C08F 5/20

[52] U.S. Cl. ......................... 502/402; 502/400; 521/30; 521/32

[58] Field of Search ............................ 502/402, 400; 521/30, 32

[56] References Cited

U.S. PATENT DOCUMENTS

| | | | |
|---|---|---|---|
| 5,037,857 | 8/1991 | Maroldo et al. | 521/29 |
| 5,079,274 | 1/1992 | Schneider et al. | 521/146 |

*Primary Examiner*—Glenn Caldarola
*Assistant Examiner*—In Suk Bullock
*Attorney, Agent, or Firm*—Ilya Zborovsky

[57] ABSTRACT

A sorbent for removing toxicants from blood or plasma includes a plurality of beads composed of hyper-crosslinked polystyrene-type resin and having a surface which is modified so as to prevent adsorption of large proteins and platelets and to minimize activation of blood complement system without affecting noticeably accessibility of an inner adsorption space of the beads for small and middle-sized toxicant molecules.

24 Claims, No Drawings

5,773,384

SORBENTS FOR REMOVING TOXICANTS FROM BLOOD OR PLASMA, AND METHOD OF PRODUCING THE SAME

BACKGROUND OF THE INVENTION

The present invention relates to sorbents for removing toxicants from blood or plasma, and also for a method of producing such sorbents.

Blood represents the most important body fluid which circulates through all organs and tissues thus supplying them with oxygen and numerous required organic and inorganic compounds and transporting carbon dioxide and harmful metabolites towards the lung and excretion organs. Blood contributes to maintaining constant temperature of the body and specific osmotic and acid-base equilibria in the organs. It carries information messengers from one organ to the others and synchronizes their cooperation. Due to the presence of antibodies, antitoxins and hydrolysing enzymes as well as the ability of leukocytes to encapsulate bacteria and small particles, blood exerts an important protecting function.

Blood consists of formulate elements (erythrocytes, leukocytes, platelets and others) and plasma. The latter contains thousands of proteins, glycoproteins, peptides, hormones and other biologically active compounds which regulate the activity of all organs. Any disease would alter composition and properties of blood since the malfunctioning organ would release wrong metabolites into blood circulation, causing harmful intoxication of other organs and the body as a whole. By removing the intoxicants from blood, general condition of a patient can be improved significantly.

The body contains about 70 ml blood per 1 kilogram of body weight, so that, on the average, about 5 l blood in a man or 4 l in a woman have to be forced to pass 2 to 4 times through the purification device. With the flow rate through the device of about 100–150 ml/min, the whole procedure would last for few hours.

Conventional procedures for the purification of blood extracorporeally include membrane techniques (hemodialysis, plasma pheresis, ultrafiltration), sorption techniques (hemoperfusion, plasma perfusion) and combinations of these methods. Hemodialysis, ultrafiltration and plasma pheresis separate compounds according to their size and do not selectively remove specified components. Sorption techniques, on the contrary, can be both selective and non-selective.

Hemoperfusion involves the passage of the contaminated blood over a solid surface of a detoxicant particulate mass that separates the contaminant by sorption or by ion exchange. Another procedure, plasma perfusion, involves separation of blood cells prior to contacting plasma with the sorbent. In any case, treated blood or both cells and treated plasma have to be returned to the patient's blood circulation system.

There are cases where the toxic components to be removed from blood are well established. In these cases, selective sorbents can be employed which incorporate ligands specially designed to attract and bind the target species. Exemplary of potential applications of selective perfusion systems are: (1) the removal of autoimmune antibodies, immunoglobulins and immune complexes using sorbents such as Protein-A; (2) removal of circulating toxins and tumor antigens (e.g., a-fetoprotein associated with hepatic cancer, carcinoembrionic antigen associated with various carcinomas, thioesterase or cytokeratins associated with breast cancer, and the like) using sorbents such as immobilized monoclonal antibodies and specific immobilized ligands; (3) removal of protein bound toxins and drugs (e.g., in the case of psychotomimetic or narcotic drug overdose) based on the antigenic properties of these protein conjugates; (4) procedures using live cells in the plasma chamber in the place of sorbents such as islet cells or liver tissue fragments for the treatment of diabetes, hepatocytes for the treatment of hepatic failure and the like; (5) selective removal of plasma components using immobilized enzymes as sorbents; (6) removal of cholesterol (low density lipoproteins, DLD) using sorbents specific to LDL; (7) removal of excess phosphate on the MgO/TiO complex deposited on active carbons; (8) adsorption of triglycerides, cholesterol and fatty acids on hydrophobic polymer materials; (9) removal of human immunodeficiency virus using calcinated hydroxyapatite-silica-alumina adsorbing materials; (10) absorbing free hemoglobin from plasma on polyphenylalanine, polyalkylene-oxide or mineral or polymeric porous materials bearing groups of tyramine, tyrosine, phenylalanine and aminophenol on the surface.

Not less frequent are cases where several toxic compounds appear in blood simultaneously, often unidentified or even unknown. These are mainly toxins of low or middle-range molecular weights. Here, selective immunoadsorbents can not be prepared in a reasonable period of time and non-selective adsorbents are needed which readily adsorb a variety of relatively small toxic molecules. Preferential adsorption is mainly caused by smaller polarity of these toxins as compared to that of natural amino acids and saccharides which are useful conventional small components of normal blood. Hydrophobic adsorbing materials, in particular activated carbon, are used as the non-selective adsorbents in these cases.

Hemoperfusion and plasma perfusion on non-specific activated carbon-type sorbents was shown to be extremely helpful in treatment of schizophrenia (Kinney, U.S. Pat. No. 4,300,551, 1981), prim. pulmonary hypertension (SU 1507-397-A, 1989), multiple sclerosis (SU 1466-754-A, 1989), treatment of rhesus-conflict in obstetrics (SU 1533-697-A, 1989), for detoxication of organism of patients who have undergone extensive surgery (SU 1487-909-A, 1989).

A perspective technique of cancer treatment is described by Bodden (U.S. Pat. No. 5,069,662, December 1991), by which high concentrations of anti-cancer agents can be perfused through a body organ containing a tumor and then removed from the organ with effluent blood. The contaminated blood is then transported to an extracorporeal circuit, purified from contaminations and returned to the body. This permits safe infusion of greater than usual concentrations of chemotherapeutic agents and delivering lethal doses of the agents to the tumor while preventing toxic levels of the agents from entering the body's general circulation. The process is applicable to the treatment of a number of tumors such as those of kidney, pancreas, bladder, pelvis and, in particular, the liver. Illustrative of suitable chemotherapeutic agents for use in the practice are Adriamycin (doxorubicin), fluorinated pyrimidines (5-fluorouracyl 5-FU or floxuridine FURD), cisplatin, Mytomycin C, cyclophosphamide, methotrexate, vincristine, Bleomycin, FAMT, and any other anti-cancer agent. Blood detoxication most effectively can be achieved by hemoperfusion through a cartridge with a non-specific sorbent, for example, activated carbon, able to clear the blood from the above antineoplastic agents.

In any hemoperfusion system, whole blood comes into direct contact with the sorbent, such as active carbon, which leads to two kinds of serious problems. First, fine carbon particles tend to be released into the blood stream to become emboli in blood vessels and organs such as lungs, spleen and kidneys. Second, the biological defense system of blood may be activated and react in several ways: the blood may coagulate to form a clot, or thrombus, the immune system may respond unfavorably, and white blood cells may act to encapsulate the artificial device. Indeed, while hemoperfusion on activated carbon was initially very effective, the previous attempt have been plagued by very high losses of white cells and platelets as well as clotting, sludging and channeling of blood in the column incorporating the adsorbent. The column then becomes ineffective and the patient suffers thrombocytopenia, in addition to severe embolia.

Therefore, many attempts have been done to prevent release of fines and to enhance the biocompatibility of the sorbents. Clark (U.S. Pat. No. 4,048,064, September 1977) describes formation of a semipermeable polymeric coating on the carbon particles by polymerization of various hydrophilic monomers, in particular hydroxyethylmethacrylate (HEMA) and acrylamide. Moreover, he includes heparin into the coating polymer, in order to minimize complement activation and aggregation of platelets. Nakashima, et al. (U.S. Pat. No. 4,171,283, October 1979) suggests to add an epoxy moiety containing comonomer, which allows post-crosslinking of the polymeric coat formed, thus enhancing the mechanical stability of the coating. However, thin hydrophilic polymeric coatings were found to "fall apart", whereas thick coatings retarded diffusion and deteriorated sorption properties of the carbon.

According to Maxid (U.S. Pat. No. 5,149,425, September 1992; U.S. Pat. No. 5,420,601, August 1993), thin integral membranes on the surface of the adsorbent can be better prepared from hydrophobic, insoluble in water polymer, like polystyrene, polysulfone, polyether urethane which are coated in an amount of 0.1–1% of the weight of matrix from a solution in an organic solvent which is added to the sorbent and then evaporated under vacuum in a rotovap. However, hydrophobic membranes prevent diffusion of toxins into the sorbent bead. Therefore, an additional, water-soluble polymer, for example polyethyleneglycol, has to be added to the system during the coating procedure (in an amount of 0.5–5% of the weight of the membrane-forming polymer), which is then eluted with water, thus leaving pores of about 20 angstroms in diameter in the main hydrophobic coating membrane.

Alternatively, activated carbon was coated with a polyelectrolyte complex prepared from a polycation (DEAE-cellulose) and heparin and precipitated on the surface of carbon beads (Valueva, et al., SU 844-569, 1981).

Besides activated carbon, porous polymeric hydrophobic materials can serve as non-selective adsorbents; they are, however, less examined. Endotoxins were observed to adsorb on porous polypropylene and polyethylene (Harris, U.S. Pat. No. 4,059,512, November 1977). Macroporous styrene-divinylbenzene copolymers were shown to be useful for blood detoxication from barbiturates and glutethimides (Kunin, et al., U.S. Pat. No. 3,794,584, February 1974).

Most powerful polymeric adsorbing materials are the hypercrosslinked styrene polymers introduced by Davankov and Tsyurupa in 1969 (Davankov, et al., SU 299165, 1969; U.S. Pat. No. 3,728,467, April 1973; Reactive Polymers, 13, 27–42, 1990). These polymers are prepared by an extensive crosslinking of polystyrene chains with rigid bifunctional crosslinking reagents in the presence of large amounts of a good, from the thermodynamic point of view, solvent. The initial polystyrene is either dissolved in or highly swollen with this solvent. The final product represents a low density polymer displaying a large inner surface area (of about 1,000 $m^2/g$), and the ability to swell with any liquid, including water. The hypercrosslinked polystyrene exhibits outstanding adsorption properties with respect to organic compounds dissolved in aqueous media (Rosenberg, et al., Reactive Polymers, 1, 175–183, 1983; Davankov, et al., Reactive Polymers, in press, 1995). This stimulated Schwachula et al. (DDR Patent 249-274-A1, 1986) to suggest polymeric adsorbents of this kind to be employed for hemoperfusion (after the possible residual chloromethyl groups being hydrolyzed with alkali or substituted with polyethylene glycol chains).

Recently, hypercrosslinked polystyrene sorbents have become available through Purolite, Int., Ltd. (UK) under the trade name "Macronet Hypersol".

There are two basic types of hypercrosslinked polystyrene sorbents: microporous with pore diameters of 1 to 1.5 nm and biporous having larger pores in addition to the above micropores. Synthesis of these materials is well documented in the scientific literature (see review papers V. A. Davankov and Tsyurupa, Pure & Appl. Chem., 161, 1881–1888, 1989; Reactive Polymers, 13, 27–42, 1990 and references therein). The both types of sorbents can be employed successfully for hemoperfusion, allowing penetration of small or both small and middle-size molecules into the interior of the sorbent beads.

While the adsorption properties of hypercrosslinked polystyrene-type sorbents towards small and middle-size organic molecules, especially those of lower polarity (like the majority of blood toxicants), are excellent, the hemocompatibility of the material required additional improvement.

SUMMARY OF THE INVENTION

Accordingly, it is an object of the present invention to provide a sorbent for removing toxicants from blood or plasma, which avoids the disadvantages of the prior art.

More particularly, it is an object of the present invention to provide a sorbent for removing toxicants from blood or plasma which is characterized by good biocompatibility.

In keeping with these objects and with others which will become apparent hereinafter, one feature of the present invention resides, briefly stated, in a sorbent for removing toxicants from blood or plasma, which has a plurality of beads of hypercrosslinked polystyrene-type resin, which beads have a surface modified so as to prevent adsorption of large proteins and platelets and to minimize activation of blood complement system, without affecting noticeably the accessability of the inner adsorption space of the beads for small and middle-size toxicant molecules.

It is another feature of the present invention to provide a method of producing the new sorbent, which includes modification of the surface of the beads of the hypercrosslinked polystyrene-type resin, such that adsorption of large proteins and platelets is prevented and activation of blood complement system is minimized without affecting noticeably the accessibility of the inner adsorption space of the beads for small and middle-size toxicant molecules.

When the sorbent is formed and produced in accordance with the present invention, the sorbent has a good biocompatibility.

The novel features which are considered as characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

In accordance with the present invention a sorbent for removing toxicants from blood or plasma is proposed, which comprises a sorbent for removing toxicants from blood or plasma, which has a plurality of beads of hypercrosslinked polystyrene-type resin, which beads have a surface modified so as to prevent adsorption of large proteins and platelets and to minimize activation of blood complement system, without affecting noticeably the accessability of the inner adsorption space of the beads for small and middle-size toxicant molecules.

Also, in accordance with the present invention, a method of producing of the sorbent is proposed which comprises the steps of modifying the surface of the beads of the hypercrosslinked polystyrene-type resin, such that adsorption of large proteins and platelets is prevented and activation of blood complement system is minimized without affecting noticeably the accessibility of the inner adsorption space of the beads for small and middle-size toxicant molecules.

Modification protocols of the beads surface are identical for microporous and biporous materials.

Several approaches are exploited to achieve the desired chemical modification of the bead surface, which are intended to enhance the hemocompatibility of the material.

One possible approach is the formation of lipid-like layers on the surface of polystyrene beads, which should simulate the structure of biomembranes. Copolymers of 2-methacryloyloxyethyle-phosphorylcholine with n-butyl-methacrylate can be grafted on the surface of materials. The copolymer was shown to adsorb free phospholipids from blood to form an organized structure similar to that of a bilayer membrane. It is believed that membrane-like surfaces are thus formed which reduce adsorption of proteins and platelets from blood and make the material more biocompatible. In our approach, groups of phosphatidylcholine are formed on the surface of polystyrene beads, without a preliminary grafting of the hydrophilic copolymer suggested by Ishihara, et al.

Second approach consists of depositing heparin on the surface of the polystyrene beads. This can be done in several ways, including (i) chemical covalent binding of heparin to the polystyrene chains on the surface of beads, or (ii) electrostatic adsorption of heparin molecules, which are negatively charged, to positively charged ionogenic groups introduced into the surface layer of the beads. Heparin inhibits activation of the blood complement system and prevents formation of cloths.

Still another approach consists of binding long hydrophilic polymer chains on the beads surface, which should prevent contacts between blood proteins and cells with the hydrophobic polystyrene surface.

Finally, the fourth approach is depositing high molecular weight fluorinated polyalkoxyphosphazene on the outer surface of the beads. Phosphazene represent the best biocompatible polymeric material. Modification of the sorbent surface consists in contacting the polystyrene beads with an appropriate amount of a solution of the polyphosphazene in an organic solvent. Due to the ability of the hypercrosslinked polystyrene to strongly swell with the solvent, the latter appears completely incorporated into the beads after a short period of time, whereas the dissolved polyphosphazene remains deposited on the surface of beads. The solvent incorporated into the beads is then removed by heating the beads under reduced pressure. The large size of polyphosphazene molecules used in this procedure prevents their penetration into the pores of the beads. Therefore, the whole of the internal surface of the material remains active and accessible to blood toxicants, whereas the outer surface exposes to blood proteins and cells the insoluble in water and biocompatible polyphosphazene.

The chemical modification of the surface of sorbent beads, which is the case in the first three of the above modification approaches, is facilitated by the remarkable peculiarity of the hypercrosslinked polystyrene, namely, that the reactive functional groups of the polymer are predominantly located on its surface. The hypercrosslinked polystyrene is generally prepared by crosslinking polystyrene chains with large amounts of bifunctional compounds, in particular, those bearing two reactive chloromethyl groups. The latter alkylate, in a two step reaction, two phenyl groups of neighboring polystyrene chains according to Friedel-Crafts reaction with evolution of two molecules of HCl and formation of a cross bridge. During the crosslinking reaction, the three-dimensional network formed acquires rigidity. This property gradually reduces the rate of the second step of the crosslinking reaction, since the reduced mobility of the pending second functional group of the initial crosslinking reagent makes it more and more difficult to find an appropriate second partner for the alkylation reaction. This is especially characteristic of the second functional groups which happen to be exposed to the surface of the bead. Therefore, of the pending unreacted chloromethyl groups in the final hypercrosslinked polymer, the largest portion, if not the majority of the groups, are located on the surface of the bead (or on the surface of large pores). This circumstance makes it possible to predominantly modify the surface of the polymer beads by involving the above chloromethyl groups into various chemical reactions which are the subject of the present invention.

The following examples are intended to illustrate, but not to limit, the invention. In general, the examples and associated preparation protocols illustrate the modification of the surface of microporous and biporous hypercrosslinked polystyrene beads prepared by an extensive crosslinking of corresponding styrene-divinylbenzene copolymers using monochlorodimethyl ether as the bifunctional reagent or using other conventional chloromethylation and post-crosslinking protocols. The content of residual pending chloromethyl groups in the polystyrene beads amount to 0.5–1.0% CL for the microporous and up to 7% for biporous materials. The beads of the initial material should preferably be spherical and smooth to minimize possible damages to hematocytes.

The sorbents prepared in accordance with this invention are charged to a column or cartridge for service. The column should preferably be provided with an inlet and an outlet designed to allow easy connection with the blood circuit, and with two porous filter set between the inlet and the sorbent layer, and between the sorbent layer and the outlet. The column may be made of a biocompatible material, glass, polyethylene, polypropylene, polycarbonate, polystyrene. Of these, polypropylene and polycarbonate are preferred materials, because the column packed with the sorbent can be sterilized (e.g., autoclave and α-ray sterilization) before use.

The column or cartridge is then filled with a 1% solution of human serum albumin in normal saline and stored at 4° C. When ready for use, the column is washed with 0.9% NaCl solution to which has been added a suitable anticoagulant. such as ACD-A containing heparin in an effective amount. For a 250 ml cartridge, this is approximately 1 l of the sodium chloride solution to which 150 ml of ACD-A containing 6,000 units of heparin has been added.

As usual the following two typical extracorporeal blood circulation systems can be employed:
  (i) Blood taken from a blood vessel of a patient is forced to pass through a column packed with the sorbent of this invention, and the clarified blood is returned to the blood vessel of the patient.
  (ii) Blood taken from a patient is first separated through a separation membrane, by centrifugation or the like into hemocytes and plasma, the plasma thus separated is then forced to pass through the column packed with the sorbent of this invention to remove toxicants from the plasma; then, the clarified plasma from the column is mixed with the hemocytes separated above, and the mixture is returned to the blood vessel of the patient.

Of these two methods, the latter is more practical because of the smaller loss of hemocytes, for example, by adhesion of platelets and erythrocytes.

Any other ways of performing hemoperfusion or plasma perfusion are appropriate with the modified sorbents of this invention. Especially promising seems to be the above mentioned suggestion of Bodden (U.S. Pat. No. 5,069,662, December 1991), by which high concentrations of anticancer agents are perfused through the liver or other body organ containing a tumor and then the effluent blood is subjected to the extracorporeal hemoperfusion to remove the excess of the drug before the blood is returned to the blood circulation system of the patient. Another perspective system is that by Shettigar, et al. (U.S. Pat. No. 5,211,850, 1993), where achieving both convective and diffusive transport of plasma across a hollow fiber membrane towards a closed chamber with a sorbent and back into the fiber channel was suggested. The chamber could be packed with the sorbent of this invention.

In general, the modified hypercrosslinked polystyrene-type sorbents of the present invention are intended to replace in hemoperfusion and plasma perfusion procedures all kinds of activated carbons. The new material is mechanically stable and does not release fines causing embolia; it is much more hemocompatible, exhibits higher sorption capacities toward a broad range of blood toxicants, and can, in principle, be regenerated and reused.

The adsorption spectrum of modified hypercrosslinked polystyrene sorbents of this invention extends to substances with molecular weights of between 100 and 20,000 daltons. The maximum adsorption is of molecules with weight of between 300 and 1,500 daltons, identified clinically as "medium molecules", which are present in abnormal quantities in ureamic and many other patients and are incompletely removed by conventional hemodialysis procedures. Such compounds as creatinine, barbiturate, phenobarbital, sodium salicylate, amphetamines, morphine sulfate, meprobamate, glutethimide, etc. can be effectively and rapidly removed from the blood using both microporous and biporous sorbents. (To avoid removal of useful drugs from blood during hemoperfusion on the new sorbents, the latter can be previously saturated with the corresponding drug to an appropriate level). In addition to removal of small and medium molecules, the biporous sorbents also shows an excellent ability to absorb cytochrom C and beta-2-microglobulin (molecular weight of about 20,000 daltons) as well as vitamin B12.

Preparation of initial hypercrosslinked polystyrene To a solution of 87.6 g xylylene dichloride (0.5 mol) in 600 ml dry ethylene dichloride 104 g (1 mol) of styrene copolymer with 0.5% divinylbenzene were added, the suspension was agitated for 1 hr and supplied with a solution of 116.8 ml tinn tetrachloride (1 mol) in 100 mol ethylene dichloride. The reaction mixture was then heated for 10 hrs at 80° C., the polymer was filtrated and carefully washed with aceton, a mixture of aceton with 0.5N HCL, 0.5N HCl and water until no chlorine ions were detected in the filtrate. The product dried in vacuum represented microporous hypercrosslinked polystyrene. It contained 0.65% pendant unreacted chlorine and displayed an inner surface area as high as 980 m$^2$/g.

To a suspension of 104 g (1 mol) of a macroporous styrene copolymer with 4% divinylbenzene in 500 ml dry ethylene dichloride a solution of 76 ml (1 mol) monochlorodimethyl ether and 116.8 ml (1 mol) tinn tetrachloride (1 mol) in 100 ml ethylene dichloride was added. The mixture was then heated at 80° C. for 10 hrs, the polymer was filtrated and carefully washed with aceton, a mixture of aceton with 0.5N HCL, 0.5N HCl and water until no chlorine ions were detected in the filtrate. The product dried in vacuum represented biporous hypercrosslinked polystyrene and contained 3.88% pendant unreacted chlorine. The above extensive crosslinking resulted in the increase of its inner surface area from 120 to 1,265 m$^2$/g.

Formation of lipid-like surface structures

EXAMPLE 1

To a dispersion of 10 g biporous polymer in 30 ml of a dioxane-methanol mixture (5:1, vol/vol) a solution of 1 g NaI and 6 ml of 2-ethanol amine in 1 ml of the same mixed solvent was added, and heated at 80° C. for 9 hrs. The polymer was filtered, washed with the dioxane-methanol mixture, methanol 0.1N HCl (in order to protonate the secondary amino groups) and finally rinsed with water and 50 ml methanol. To the polymer, dried in vacuum, 25 ml of dry pyridine were added and then 1 ml POCl$_3$ in 5 ml dry pyridine. The reaction mixture was kept for 15 hrs at ambient temperature, filtered, the polymer was rinsed with dry pyridine and with a solution of 1.4 g choline chloride in 25 ml dry dimethyl sulfoxide at 40° C. The mixture was heated to 60° C. for 4 hrs, kept at ambient temperature for 15 hrs, provided with 5 ml dry pyridine and, after additional 5 hrs washed carefully with distilled water and rinsed with ethanol. The resin was kept in ethanol at 5° C. before use.

Microporous hypercrosslinked polymer was modified by exactly the same procedure.

EXAMPLE 2

3 g of the biporous polymer modified with 2-ethanol amine and activated with POCl$_3$ as described in Example 1 were treated with a solution of 0.3 g tert.-butyl-oxycarbonyl-L-serine in 2 ml dry pyridine at ambient temperature for 15 hrs, washed with ethyl acetate, dioxane, water and methanol and then dried. The protecting BOC-groups were removed with 5 ml trifluoroacetic acid in 1 hr at ambient temperature. The final product was washed with ether, ethanol and water.

Microporous hypercrosslinked polymer was modified by exactly the same procedure.

EXAMPLE 3

4 g of the biporous hypercrosslinked polymer were allowed to swell with 16 ml of an 8% solution of NaOH in ethylene glycol and then heated to 180° C. for 5 hrs, in order to substitute the residual chloromethyl groups with ethylene glycol groups. The polymer was washed with ethanol, water, acetone and dried under vacuum. The dry polymer was then activated with $POCl_3$ and reacted with choline chloride as described in Example 1.

Microporous hypercrosslinked polymer was modified by exactly the same procedure.

EXAMPLE 4

4 g of the biporous hypercrosslinked polymer were modified with ethylene glycol as described in Example 13, activated with $POCl_3$ as described in Example 1 and reacted with a mixture of 3 ml glacial acetic acid and 3 ml 2-ethanol amine at ambient temperature for 3 days. The product was washed with pyridine, water and ethanol.

Microporous hypercrosslinked polymer was modified by exactly the same procedure.

Depositing heparin on the surface

EXAMPLE 5

The product of reacting the initial biporous polymer with 2-ethanol amine according to Example 1 was washed with 0.5 1 0.1N HCl and water, provided with 5 ml of aqueous heparin solution (5,000 U/ml) and kept for 15 hrs at ambient temperature and for 4 hrs at 5° C. The polymer with the ionically adsorbed heparin was filtered from the excess solution and kept in ethanol at 5° C. before use.

Microporous hypercrosslinked polymer was modified by exactly the same procedure.

EXAMPLE 6

The heparin adsorbed on the polymer according to Example 5 was bonded covalently by treating the polymer for 4 hrs with an aqueous solution of glutare dialdehyde (2.0 ml of a 25% solution for 1 g of the wet polymer). The pendant aldehyde groups were coupled then with L-aspartic acid (0.2 g L-Asp in 3 ml 1N NaOH for 1 g polymer) for 14 hrs. The polymer washed with 0.1N NaOH and water was kept in ethanol at 5° C. before use.

Microporous hypercrosslinked polymer was modified by exactly the same procedure.

EXAMPLE 7

The heparin adsorbed on the polymer according to Example 5 was bonded covalently by washing the polymer with 500 ml dry methanol, 200 ml dry dioxane and treating it for 5 hrs with a solution of 0.1 g hexamethylene diisocyanate in 3 ml dioxane (for 1 g polymer). The polymer was filtered, washed with dioxane and the pendant isocyanate groups coupled with L-aspartic acid by treating the polymer with 1 g tris-trimethylsilyl derivative of L-Asp in 3 ml heptane for 15 hrs at ambient temperature. The polymer was washed with heptane, methanol, 0.1N NaOH and water and kept in ethanol at 5° C. before use.

Microporous hypercrosslinked polymer was modified by exactly the same procedure.

EXAMPLE 8

1 g of the product of reacting the initial biporous polymer with 2-ethanol amine according to Example 1 was washed with water and treated with 4 ml 25% aqueous solution of glutare dialdehyde for 5 hrs at ambient temperature. Excess of the reagent was then removed with water and the polymer was supplied with 2.5 ml of heparin solution (5,000 U/ml) for 15 hrs at ambient temperature and finally rinsed with water.

Microporous hypercrosslinked polymer was modified by exactly the same procedure.

EXAMPLE 9

1 g of the product of reacting the initial biporous polymer with 2-ethanol amine according to Example 1 was washed with methanol, dried in vacuum, swelled with dioxane and supplied with a solution of 0.1 g hexamethylene diisocyanate in 3 ml dioxane. After 10 hrs. the product was washed with dry dioxane and dimethyl sulfoxide and treated with 2.5 ml of an aqueous solution of heparin (5,000 U/ml) for 3 days. The excess heparin was removed with water and the polymer was kept in ethanol at 5° C. before use.

Microporous hypercrosslinked polymer was modified by exactly the same procedure.

Modification with hydrophilic polymers

EXAMPLE 10

1 g of the product of reacting the initial biporous polymer with 2-ethanol amine and activating it with glutare dialdehyde according to Example 8 was treated with 2 ml aqueous solution of 0.16 g polyethylene glycol (molecular weight 20,000) for 3 days at ambient temperature and then carefully washed with water.

Microporous hypercrosslinked polymer was modified by exactly the same procedure.

EXAMPLE 11

1 g of the product of reacting the initial biporous polymer with 2-ethanol amine and activating it with hexamethylene diisocyanate according to Example 9 was treated with 2 ml aqueous solution of 0.16 g polyethylene glycol (molecular weight 20,000) for 3 days at ambient temperature and then carefully washed with water.

Microporous hypercrosslinked polymer was modified by exactly the same procedure.

EXAMPLE 12

4 g of biporous hypercrosslinked polymer was allowed to swell with 16 ml of an 8% solution of NaOH in ethylene glycol and then heated to 180° C. for 5 hrs, in order to substitute the residual chloromethyl groups with ethylene glycol groups. The polymer was washed with ethanol, water, aceton and dried under vacuum. 2 g of dry polymer, swollen with dry dioxane, were activated with hexamethylene diisocyanate as described in Example 9, washed with dry dioxane and supplied with a solution of 1.2 g polyethylene glycol (molecular weight 40,000) in 10 ml dry dimethyl sulfoxide, heated at 80° C. for 6 hrs and washed with ethanol and water.

Microporous hypercrosslinked polymer was modified by exactly the same procedure.

EXAMPLE 13

2 g of the ethylene glycol-modified polymer prepared according to Example 12 were activated with glutare dialdehyde according to the procedure described in Example 8 and treated with a solution of 1.2 g polyethylene glycol (molecular weight 40,000) in 10 ml water for 1 day at ambient temperature. The polymer was washed then with ethanol and water.

Microporous hypercrosslinked polymer was modified by exactly the same procedure.

EXAMPLE 14

To 3 g of dry biporous polymer, swollen with dry benzene, were added 15 ml of a solution containing 8 g alcoholate of polyethylene glycol (molecular weight 12,000) in dry benzene and the mixture was boiled under an argon atmosphere and adding small pieces of sodium as long as the latter dissolved in the reaction mixture (about 10 hrs). After additional two days at room temperature, the polymer was carefully washed with ethanol.

Microporous hypercrosslinked polymer was modified by exactly the same procedure.

EXAMPLE 15

According to the procedure described in Example 14, 1 g of the polymer were treated with 1 g of the alcoholate of polyethylene glycol of lower molecular weight (6,000).

EXAMPLE 16

To a solution of 0.2 g polyethylene glycol (molecular weight 12,000) in 4 ml dry benzene were added first 0.1 ml of hexamethylene diisocyanate and then, after 2 hrs, 2 g of dry biporous polymer which was previously modified with ethylene glycol according to the procedure described in Example 12.

Microporous hypercrosslinked polymer was modified by exactly the same procedure.

EXAMPLE 17

Procedure described in Example 16 was repeated with polyethylene glycol of lower molecular weight (6,000).

EXAMPLE 18

0.2 g chitosan were dissolved in 6 ml concentrated acetic acid and added to 2 g of dry biporous polymer. After 2 hrs, 10 ml of cold 30% NaOH solution were slowly added to the above mixture, the polymer was separated from the reaction mixture, rinsed with water, dehydrated with methanol, dried and heated to 80° C. with 10 ml of a solution of 0.1 g NaI in a dioxane-methanol mixture (5:1, vol/vol) for 8 hrs, in order to accomplish alkylation of the chitosan amino groups by chloromethyl groups of the polymer. The final product was washed with aqueous acetic acid and then ethanol.

Microporous hypercrosslinked polymer was modified by exactly the same procedure.

Coating with phosphazene

EXAMPLE 19

A solution of 0.0009 g poly(trifluoroethoxy) phosphazene (molecular weight $10^7$) in 8 ml ethyl acetate were added quickly to 3 g of dry biporous polymer and agitated until the whole of the solvent was totally absorbed by the polymer beads. The material was then dried under reduced pressure and washed with ethanol.

It will be understood that each of the elements described above, or two or more together, may also find a useful application in other types of products and methods differing from the types described above.

While the invention has been illustrated and described as embodied in a sorbent for removing toxicants from blood or plasma, and method of producing the same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters patent is set forth in the appended claims:

1. A sorbent for removing toxicants from blood or plasma, comprising a plurality of beads composed of hypercrosslinked polystyrene resin and having a surface which is modified, wherein said surface of the beads comprising deposited high molecular weight poly (N-trifluoroalkoxy) phosphazene, deposited by treating the beads with a solution of phosphazene in an organic solvent and evaporating the solvent.

2. A sorbent as defined in claim 1, wherein said beads are modified microporous hypercrosslinked polystyrene beads prepared through an extensive crosslinking of gel styrene-divinylbenzene copolymer beads.

3. A sorbent as defined in claim 1, wherein said beads are modified biporous hypercrosslinked polystyrene beads prepared through an extensive crosslinking of macroporous styrene-divinylbenzene copolymer beads.

4. A sorbent as defined in claim 1, wherein said beads are modified beads of styrene-divinylbenzene copolymers subjected to an extensive crosslinking in a swollen state with bifunctional crosslinking agents.

5. A sorbent as defined in claim 4, wherein said bifunctional crosslinking agent is an agent selected from the group consisting of monochlorodimethyl ether and p-xylylene dichloride.

6. A sorbent as defined in claim 1, wherein said beads are modified beads of styrene-divinylbenzene copolymers subjected to chloromethylation and post-crosslinking.

7. A sorbent for removing toxicants from blood or plasma, comprising a plurality of beads composed of polystyrene hypercrosslinked resin and having a surface which is modified; and heparin electrostatically binded from an aqueous solution onto the beads with chloromethyl groups substituted by amino functions through a reaction with an amine.

8. A sorbent as defined in claim 7, wherein the chloromethyl groups are substituted by amino functions through a reaction with 2-ethanol amine.

9. A sorbent for removing toxicants from blood or plasma, comprising a plurality of beads composed of polystyrene resin and having a surface which is modified, the surface of the beads comprising 2-ethanol amine ligands substituting chloromethyl groups, heparin covalently binded to the ligands via a material selected from the group consisting of a glutare dialdehyde and hexamethylene diisocyanate moiety; and L-aspartic acid coupled with groups selected from a group consisting of excessive pendant aldehyde groups and excessive isocyanate groups.

10. A sorbent for removing toxicants from blood or plasma, comprising a plurality of beads composed of hypercrosslinked polystyrene resin and having a surface which is modified, the surface of the beads comprising a material selected from the group consisting of 2-ethanol amine ligands and ethylene glycol ligands which substitute chloromethyl groups and activated With a material selected from the group consisting of glutare dialdehyde and hexamethylene diisocyanate with hydrophilic polyethylene glycol chains covalently binded.

11. A sorbent for removing toxicants from blood or plasma, comprising a plurality of beads composed of hypercrosslinked polystyrene resin and having a surface which is modified, the surface of the beads comprises hydrophilic polyethylene glycol chains covalently binded through reacting of sodium alcoholates of the chains with polystyrene chloromethyl groups.

12. A sorbent for removing toxicants from blood or plasma, comprising a plurality of beads composed of hypercrosslinked polystyrene resin and having a surface which is modified, the surface of the beads comprising hydrophilic chains of chitosan covalently binded through reacting of amino groups of the chitosan with polystyrene chloromethyl groups.

13. A sorbent for removing toxicants from blood or plasma, comprising a plurality of beads composed of hypercrosslinked polystyrene resin and having a surface which is modified, the surface of the beads comprising ligands selected from the group consisting of 2-ethanol amine ligands and ethylene glycol ligands which substitute chloromethyl groups and activated with phosphorus oxychloride, and covalently binded hydrophilic moieties selected from the group consisting of choline, serine and 2-ethanol amine.

14. A method of producing a sorbent for removing toxicants from blood or plasma, comprising the steps of providing a plurality of beads of hypercrosslinked polystyrene resins; and modifying a surface of the beads, said modifying including depositing on the surface of the beads high molecular weight poly (N-trifluoroalkoxy) phosphazene, by treating the beads with a solution of phosphazene in an organic solvent and evaporating the solvent.

15. A method as defined in claim 14, wherein said beads are modified beads of styrene-divinylbenzene copolymers subjected to an extensive crosslinking in a swollen state with bifunctional crosslinking agents.

16. A method as defined in claim 15, wherein said bifunctional crosslinking agent is an agent selected from the group consisting of monochlorodimethyl ether and p-xylene dichloride.

17. A method as defined in claim 14, wherein said beads are modified beads of styrene-divinylbenzene copolymers subjected to chloromethylation and post-crosslinking.

18. A method of producing a sorbent for removing toxicants from blood or plasma, comprising the steps of providing a plurality of beads hypercrosslinked of polystyrene resins; and modifying a surface of the beads, said modifying including electrostatically binding of heparin from its aqueous solution onto the beads whose chloromethyl groups have been substituted by amino functions through a reaction with an amine.

19. A method as defined in claim 20, wherein said amine is 2-ethanol amine.

20. A method of producing a sorbent for removing toxicants from blood or plasma, comprising the steps of providing a plurality of beads of hypercrosslinked polystyrene resins; and modifying a surface of the beads, said modifying including substituting chloromethyl groups on the surface of the beads with 2-ethanol amine ligands and covalently binding heparin to the ligands via a material selected from the group consisting of a glutare dialdehyde and hexamethylene diisocyanate moiety and coupling groups selected from the group consisting of excessive pendant aldehyde groups and isocyanate groups with L-aspartic acid.

21. A method of producing a sorbent for removing toxicants from blood or plasma, comprising the steps of providing a plurality of beads of hypercrosslinked polystyrene resins; and modifying a surface of the beads, said modifying including substituting chloromethyl groups with a material selected from the group consisting of 2-ethanol amine and ethylene glycol ligands, activating the ligands with a material selected from the group consisting of glutare dialdehyde and hexamethylene diisocyanate, and covalently binding hydrophilic polyethylene glycol chains.

22. A method of producing a sorbent for removing toxicants from blood or plasma, comprising the steps of providing a plurality of beads of hypercrosslinked polystyrene resins; and modifying a surface of the beads, said modifying including covalently binding hydrophilic polyethylene glycol chains through reacting of sodium alcoholates of the latter with polystyrene chloromethyl groups.

23. A method of producing a sorbent for removing toxicants from blood or plasma, comprising the steps of providing a plurality of beads of hypercrosslinked polystyrene resins; and modifying a surface of the beads, said modifying including covalently binding hydrophilic chains of chitosan through reacting of amino groups of the latter with polystyrene chloromethyl groups.

24. A method of producing a sorbent for removing toxicants from blood or plasma, comprising the steps of providing a plurality of beads of hypercrosslinked polystyrene resins; and modifying a surface of the beads, said modifying including substituting chloromethyl groups with ligands selected from the group consisting of 2-ethanol amine ligands or ethylene glycol ligands, activating the ligands with phosphorus oxychloride, and covalently binding hydrophilic moieties selected from the group consisting of choline, serine and 2-ethanol amine.

* * * * *